US007884301B2

(12) United States Patent
Kirstein et al.

(10) Patent No.: US 7,884,301 B2
(45) Date of Patent: Feb. 8, 2011

(54) DEVICE AND METHOD FOR SEPARATION OF MICROPARTICLES IN PARTICULAR BIOHAZARDOUS AND HAZARDOUS MATERIALS

(75) Inventors: Uwe Kirstein, Essen (DE); Klaus Lennartz, Essen (DE)

(73) Assignee: Universität Duisburg Essen, Essen (DE)

( * ) Notice: Subject to any disclaimer, the term of this patent is extended or adjusted under 35 U.S.C. 154(b) by 461 days.

(21) Appl. No.: 11/921,360

(22) PCT Filed: Jun. 2, 2006

(86) PCT No.: PCT/EP2006/005302

§ 371 (c)(1),
(2), (4) Date: Nov. 30, 2007

(87) PCT Pub. No.: WO2006/128723

PCT Pub. Date: Dec. 7, 2006

(65) Prior Publication Data

US 2009/0127167 A1    May 21, 2009

(30) Foreign Application Priority Data

Jun. 2, 2005   (DE) .................. 20 2005 008 763

(51) Int. Cl.
*B07C 5/00*    (2006.01)
*B01L 1/00*    (2006.01)
(52) U.S. Cl. .................. 209/576; 422/101; 422/104
(58) Field of Classification Search ............ 209/3.1, 209/576; 422/99, 101, 104; 435/4; 436/63
See application file for complete search history.

(56) References Cited

U.S. PATENT DOCUMENTS

| 3,963,606 | A | * | 6/1976 | Hogg .............................. 209/3 |
| 4,111,753 | A | * | 9/1978 | Folsom et al. .................. 435/3 |
| 4,230,031 | A | * | 10/1980 | Pedroso et al. ................. 454/56 |

(Continued)

FOREIGN PATENT DOCUMENTS

WO    WO 00/05566    2/2000

(Continued)

OTHER PUBLICATIONS

International Search Report for PCT/EP2006/005302, Sep. 28, 2006.

*Primary Examiner*—Joseph C Rodriguez
(74) *Attorney, Agent, or Firm*—Rankin, Hill & Clark LLP

(57) ABSTRACT

A device and method for sorting microparticles including a nozzle for a separating stream, with a vibration generator for the dispersion of the separation flow into a droplet flow with a deflector device for separation of the droplet flow into a through flow and at least one side flow depending on signals from an analytical device configured to analyze the microparticles (s) contained in the droplets and to control the deflector device. Also provided is a protective chamber in which at least the nozzle, the oscillation generator and the deflector device are arranged. The analytical device is outside the safety cabinet wherein the protective chamber is part of the safety cabinet with a clean chamber and a monitoring device through which the signals of the microparticles arising from the separating stream are supplied to the detectors of the analytical device, arranged outside the safety cabinet.

4 Claims, 4 Drawing Sheets

U.S. PATENT DOCUMENTS

| | | | |
|---|---|---|---|
| 4,279,345 A * | 7/1981 | Allred | 209/3.2 |
| 5,083,558 A * | 1/1992 | Thomas et al. | 128/202.12 |
| 5,316,560 A * | 5/1994 | Krone-Schmidt et al. | 55/385.2 |
| 5,641,457 A | 6/1997 | Vardanega et al. | |
| 5,776,781 A * | 7/1998 | Vardanega et al. | 436/63 |
| 6,010,400 A * | 1/2000 | Krainiak et al. | 454/187 |
| 6,382,228 B1 * | 5/2002 | Cabuz et al. | 137/10 |
| 6,632,260 B1 * | 10/2003 | Siemers et al. | 55/385.2 |
| 6,881,580 B2 * | 4/2005 | Hall et al. | 436/63 |
| 6,960,244 B2 * | 11/2005 | Lehman | 95/273 |
| 7,355,696 B2 * | 4/2008 | Mueth et al. | 356/244 |
| 2004/0100268 A1 * | 5/2004 | Sanders et al. | 324/453 |

FOREIGN PATENT DOCUMENTS

| | | |
|---|---|---|
| WO | WO 01/85088 A1 | 11/2001 |
| WO | WO 03/062796 A1 | 7/2003 |

* cited by examiner

DEVICE AND METHOD FOR SEPARATION OF MICROPARTICLES IN PARTICULAR BIOHAZARDOUS AND HAZARDOUS MATERIALS

TECHNICAL FIELD OF THE INVENTION

The invention concerns a device for sorting fine particle materials, called in the following microparticles. Sorting devices of this kind are used nowadays in so-called flow cytometry to sort biological materials, especially in the form of cells, such as, for example, lymphocytes or stem cells. For this purpose, a fluidic sorting stream is formed, which is formed in a nozzle as a fine fluid stream and is delivered by it. A vibration generator impinges the sorting stream in the area of the nozzle with a high-frequency vibration, which causes the sorting stream to exist only for a short distance as cohesive fluid stream and causes it to increasingly constrict in time with the vibrations at regular intervals until the sorting stream changes into a droplet stream. Individual droplets receive different electric charges from a measurement and evaluation unit in dependence upon the sorting criterion, and are deflected to the side into an electric field that is orientated transversely with respect to the vertical flow direction, in such a way that each individual droplet can be deflected in a different direction. In this way, the droplet stream is divided into a non-deflected throughflow of non-sorted droplets and at least one side stream of sorted droplets. A sheath stream, into which the microparticles are as a rule introduced shortly ahead of the delivery nozzle, is used to form the sorting stream. The sorting signal, which determines if a droplet will be discarded, that is, if it will remain in the throughflow, or if the droplet will be deflected to the side in a specific direction and will form a corresponding side stream together with equally deflected droplets, receives the direction of deflection from an evaluation device, which analyzes the sorting stream with regard to the presence of specific characteristics/parameters. The microparticles to be sorted are distributed in the sorting stream in such a way that they are arranged individually one after the other and each droplet of the droplet stream that forms from the sorting stream contains if possible one of these particles.

TECHNICAL BACKGROUND OF THE INVENTION

Sorting devices of the kind described above have been know for a long time as cell sorting devices, for example, those distributed by the Becton Dickinson Company in different models. In these known cell sorters, an optical and electronic evaluation unit is used for particle analysis. Therein, the sorting stream flows through one or several laser light beams. The light, which is scattered by the cells to be sorted, or the fluorescence signals coming out of them are observed and analyzed by the optical evaluation unit.

In the sorting method mentioned above, drops within the order of magnitude of 40-200 μm and satellite drops with diameters within the range of 3-7 μm are formed. If these drops hit against collection receptacles or against objects, droplet splashes and particulate matter of different sizes are formed. While the drops with a diameter greater than 80 μm settle relatively fast from the air, smaller drops can remain suspended for a long time (especially by means of currents) in the air as particulate matter. This particulate matter is only partially drawn off, while a protective wall is provided between the point of origin of these fine droplets, particulate matter, and the operator. In a cell sorting device with an additional protective device pursuant to WO 0185088 A1, the particulate matter is drawn off upward out of a safety chamber and is retained by means of a HEPA filter. The safety housing, which initially does not have a rear wall, is positioned in this system over the front face of a cell sorter and is sealingly connected thereto at the peripheral edge of its rear side. It was discovered that these safety measures are not always sufficient, for example, when the substances to be sorted are eventually toxic substances and/or biohazardous materials, for whose handling have to be ensured higher safety standards. Just like with the personnel protection, a special protection is simultaneously required furthermore in an increasing number of applications in order to protect, for example, lymphocytes or stem cells from contamination and/or to sort genetically modified organisms according to the specifications of the Genetic Engineering Law.

U.S. Pat. No. 6,780,277 B2 discloses an environment protection system with the object of both protecting the particles treated in the flow cytometer from contaminants as well as also protect the operators of the flow cytometer from the particles to be treated. For this purpose, some parts of a flow cytometer are arranged inside of a housing, while other parts, for example, the evaluation units, can be provided on the outside of the housing. The detector system and other monitoring means can likewise be arranged outside of the housing. A throughflow system is also provided for the housing in order to maintain a specific gas atmosphere within the housing.—A system such as this is neither suitable nor safe enough for the practical laboratory activity or economic recovery of particles to be protected and/or potentially hazardous particles.

DESCRIPTION OF THE INVENTION

It is an object of the invention to improve the safety of persons and products during the sorting of microparticles, especially when sorting biohazardous or other potentially hazardous materials.

In order to attain this object is proposed a device with the features of claim 1 and a method with the features of claim 19. The invention is based on the basic idea of docking and functionally dividing a sorting system on a microbiological safety cabinet (msc) in such a way that the laminar HEPA-filtered supply air flow guided through the clean room is disturbed as little as possible and the required strict safety conditions for microbiological safety cabinets are followed. Safety cabinets are technical work appliances destined for activities with biological work materials and especially comply with the management criteria of national and international standards (BS 5726, DIN EN 12469, and NSF standard 49). According to the invention, the functional division of the sorting device to be docked on the microbiological safety cabinet is carried out in such a way that a sorting head of the sorting device consisting of at least a delivery nozzle, a vibration generator, and a deflection device is arranged inside the microbiological safety cabinet, that is, inside of its clean room area, and the evaluation device, and preferably also the optical evaluation device for the observed light beam and/or for the excitation light, are arranged essentially outside of the microbiological safety cabinet. Both areas of the sorting device are connected in such a way that a monitoring device, for example, in the shape of a window, is provided in a side wall of the microbiological safety cabinet, whereby the imaging of the sorting stream and essential parts of the evaluation device can be monitored. According to the invention, the sample supply, the formation of the sorting stream and the droplet stream, as well as its division into partial streams is carried out within the clean room. On the other hand, the evaluation device, preferably an optical and electronic evaluation device, can be installed and the excitation laser(s) can be docked on a side wall of the microbiological safety cabinet. The sorting device as well as the adjusting elements of the laser excitation or the optical measured value acquisition can be operated by the operator within the clean room of the microbiological safety cabinet or from the front side of the sorting system outside of the clean room.

The safety criteria of a class II microbiological safety cabinet as well as also the quality requirements of a high-quality sorting performance of the sorting device are surprisingly met by means of this separation. It is especially possible by means of the invention to satisfy the high safety standards, for example, when handling toxic materials, pathogenic organisms, or also those of the cGMP standard for current Good Medical Practice. Even high-speed cell sorting ("High Speed Sorting") can thus be carried out under sterile conditions with the laminar air flow required therefor in the clean room area, while complying with the criteria of class II microbiological safety cabinets. The invention makes possible to safely prevent an uncontrolled contamination of the, cell sorting device and limit the propagation of potentially hazardous particulate matter over a narrow defined area, whose air supply makes possible the discharge of particulate matter via the exhaust channel to HEPA filters.

In order to optimize the personnel safety, a first and a second safety zone are provided in the clean room of the microbiological safety cabinet, while the sorting head is located in the first safety zone. A collecting tray can be provided under the sorting head in the first safety zone. The latter is preferably connected to an underpressure device provided outside of the clean room and a collecting tray for waste fluid arranged outside of the clean room. A collecting funnel that extends closely to the sorting head can reduce the height of the fall of the droplets and can prevent the formation of particulate matter upon impact. Into the first safety zone are drawn off, aside from the droplets, above all also the formed particulate matter. For this purpose, the suction tray is preferably surrounded by exhaust air openings in the base plate of the microbiological safety cabinet, wherein the particulate-matter is drawn into the suction channel of the microbiological safety cabinet and is retained via the terminal HEPA filter. The second safety zone that preferably (entirely or partially) encloses the first safety zone serves for the sample preparation and/or for the first steps of the further processing of the product.

In both safety zones, a laminar downwardly directed air flow (LAF) generates an overpressure that is sufficient to protect the product, wherein the suction streams that purge the air are produced on the clean room floor and the personnel protection is thus simultaneously ensured.

A further important aspect of the invention for the expansion of the sorting functions as well as for the improvement of the personnel and product safety concerns the vibration-damped installation of the parts of the sorting head that are to be provided inside the clean room, including the so-called optical bench. The latter is achieved according to the invention by vibration-damping one side wall or a separate side wall of the microbiological safety cabinet, which accommodates the sorting head and preferably also the optical bench. In this way, the possible influence of the blower that is fixedly mounted in microbiological safety cabinets, which is usually necessary for the required air circulation and air filtration, is reduced. A particularly high personnel safety is achieved by docking the sorting device on the rear wall of the microbiological safety cabinet located on the rear side of the clean room opposite to the work position of the operator, that is, behind two suction zones.

In order to avoid disturbing the sorting and droplet stream through the laminar air flow, the sorting head inside the clean room, which is preferably enclosed by a housing, is open on the bottom.

When a common carrier is provided for the sorting head, the optical bench, and the signal detection, this carrier is guided through a side wall or a separate partial wall. The part of the separate partial wall likewise accommodates the monitoring equipment. The latter can be in the simplest case a window, which allows the monitoring of, for example, the laser adjustment. The optical signals are guided outwardly to detectors from the inside of the clean room by means of a mobile and especially sealed objective system of the optical bench. The most different optical, optoelectric, acoustic, optoacoustic, and other signals released by microparticles can basically be guided out of a clean room system such as this by means of an arrangement such as this, while the device according to the invention is overall predominantly independent from a very specific sorting device type.

The signal generation device, which consists preferably, as mentioned above, of one or several lasers whose light beam(s) are preferably directed by means of mirrors/prisms through the optical bench onto the sorting stream, is preferably arranged outside of the clean room in order to keep the potentially endangered space inside the microbiological safety cabinet as small as possible, and in order to keep the laminar air flow required therein predominantly stable. In the invention, the exiting laser beam is preferably guided through a side wall, such as, for example, through a window of the microbiological safety cabinet. This can be carried out, if desired, in the area of the above-mentioned special partial wall and the docking of the sorting device on the microbiological safety cabinet can be simplified in this way. A functional separation of the optical beam path takes place in this way, in that only the monitoring point is arranged on the sorting stream within the clean room.

In order to still make possible the air suction on the microbiological safety cabinet despite the docking of the sorting device, the suction is not carried out as usual in the direction of the rear side, but via one of the two front faces of the microbiological safety cabinet.

In order to ensure uniform pressure conditions and an undisturbed laminar air flow inside the clean room, the suction cross section in the floor area of the clean room of the microbiological safety cabinet is narrowed toward the suction side. This is achieved by means of a cross section reduction of the air passage openings in the clean room floor or by means of a narrowing of the cross section of the suction channel arranged under the clean room floor in the direction of the suction side.

In the wall of the clean room can be provided in addition feedthrough openings in the shape of wall feedthroughs in order to allow optical signals, mechanical manipulators, fluids, and/or gases to enter and exit. In this way, allowances are made for the safety aspect, the demands for sterility conditions, and/or the low turbulence of the laminar air flow in the microbiological safety cabinet.

The aforementioned as well as the claimed components, which are described in the exemplary embodiments and which are to be used according to the invention, are not subjected to any special exceptions with regard to their size, shape, material selection, and technical conception, so that the selection criteria known from the application field can be applied without limitations.

Further details, features, and advantages of the object of the invention are disclosed in the dependent claims, as well as in the following description of the corresponding drawing and table, in which (as an example) an exemplary embodiment of a device for sorting microparticles is represented.

BRIEF DESCRIPTION OF THE INVENTION

In the drawings

Figure 1:
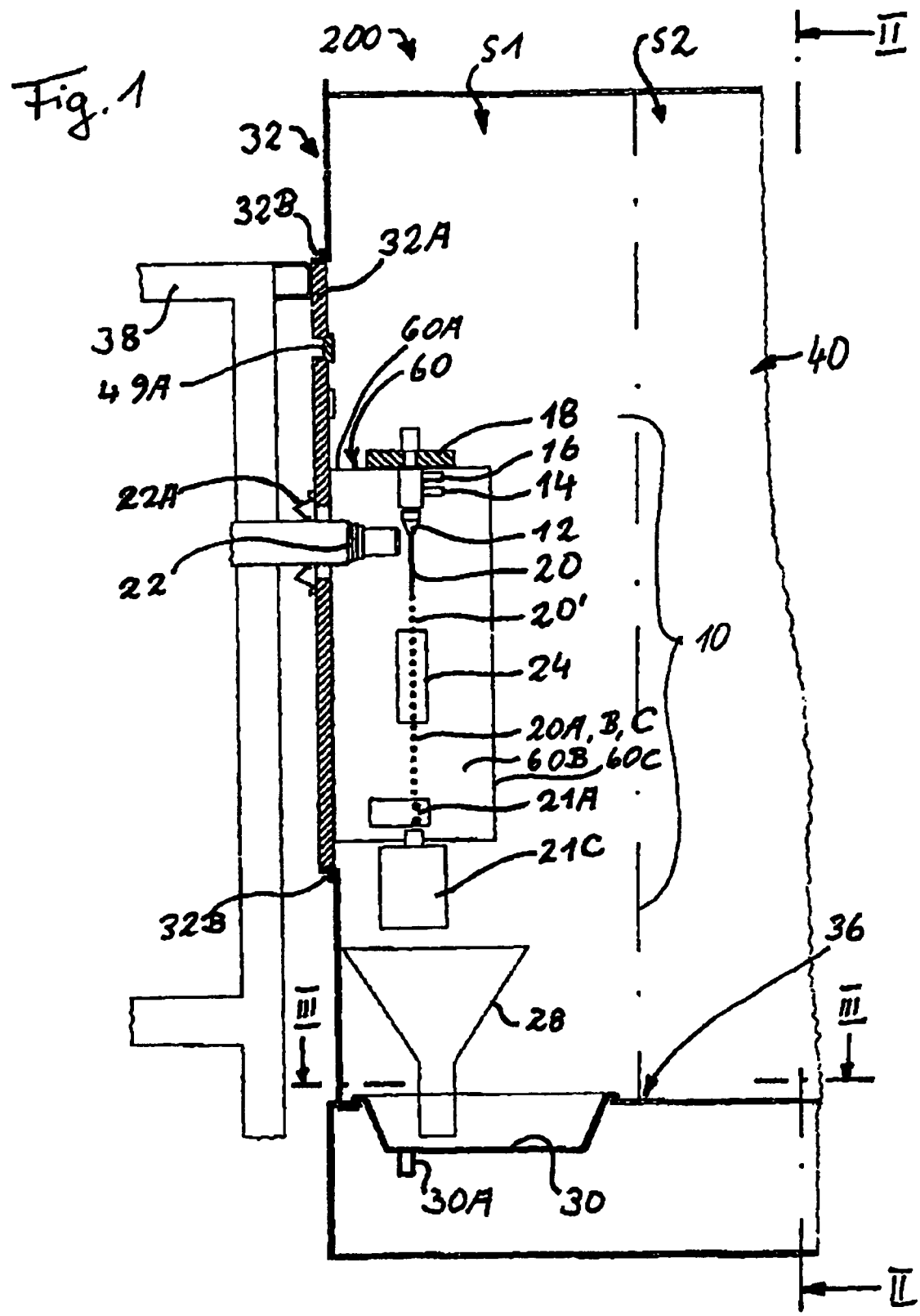
FIG. 1 shows a section of the sorting device in the area of the sorting head represented in vertical section (section along the line I-I of FIGS. 2 and 3)

In FIG. 1 can be seen the sorting head 10 of a sorting system 100 (FIG. 3) according to a cytometry process. For reasons of clarity, only the essential components are shown, namely a supply nozzle 12 in a design known per se, which feeds a sheath fluid 14 in a known manner via a hose line from a sample feeding device 50 as well as a particle stream 16 of fine particles to be sorted, which is introduced via a further hose line. A vibration generator 18 causes the nozzle 12 to vibrate with axially directed high-frequency vibrations. The sorting stream 20 supplied by the nozzle 12 is observed directly below the nozzle by means of a monitoring device 22. In this case, this takes place by means of the monitoring at the intersection point of the sorting stream and the excitation light, which originates from laser light sources (not shown), which are known per se and generate light signals, for example, scattered light signals. The monitoring device 22 is likewise the end point of an optical bench accommodated outside of the clean room 40 (which is described again below).

Figure 2:
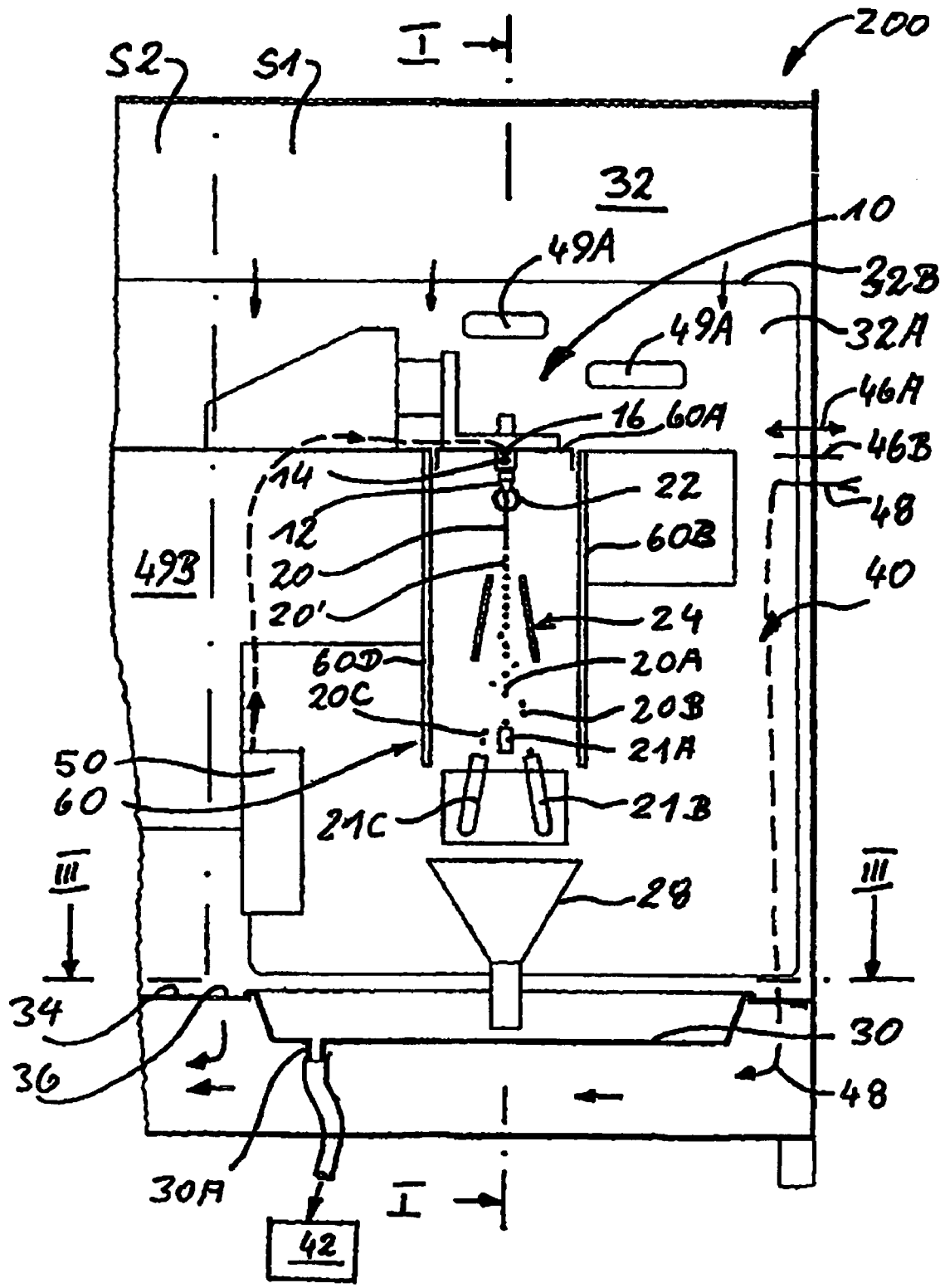
FIG. 2 shows a front view of the same sorting head represented in vertical section (section along the line II-II of FIGS. 1 and 3)

The sorting stream 20 is divided into droplets through the generation of vibration, which form a droplet stream 20' and are then guided by means of a deflection device 24 in the form of two diverging known capacitor plates, so that the droplet stream 20' is divided into a throughflow 20A and at least one side stream 20B or, according to FIG. 2, into two side droplet streams 20B and 20C. Herein, as is likewise not shown, also a division into more than two side droplet streams is possible. The throughflow 20A is drawn off into a suction tube 21A, while the side streams are collected in the collection receptacles 21B and 21C. Underneath the sorting head and the collection devices is mounted the collecting funnel 28 for the purpose of collecting eventually falling drops and preventing their splashing. The fluid collected in the funnel is discharged via a tray 30 with suction connection 30A. The tray 30 is located underneath the sorting head 10 and is fluidically connected via the suction connection 30A to a suction mechanism 42.

Figure 3:
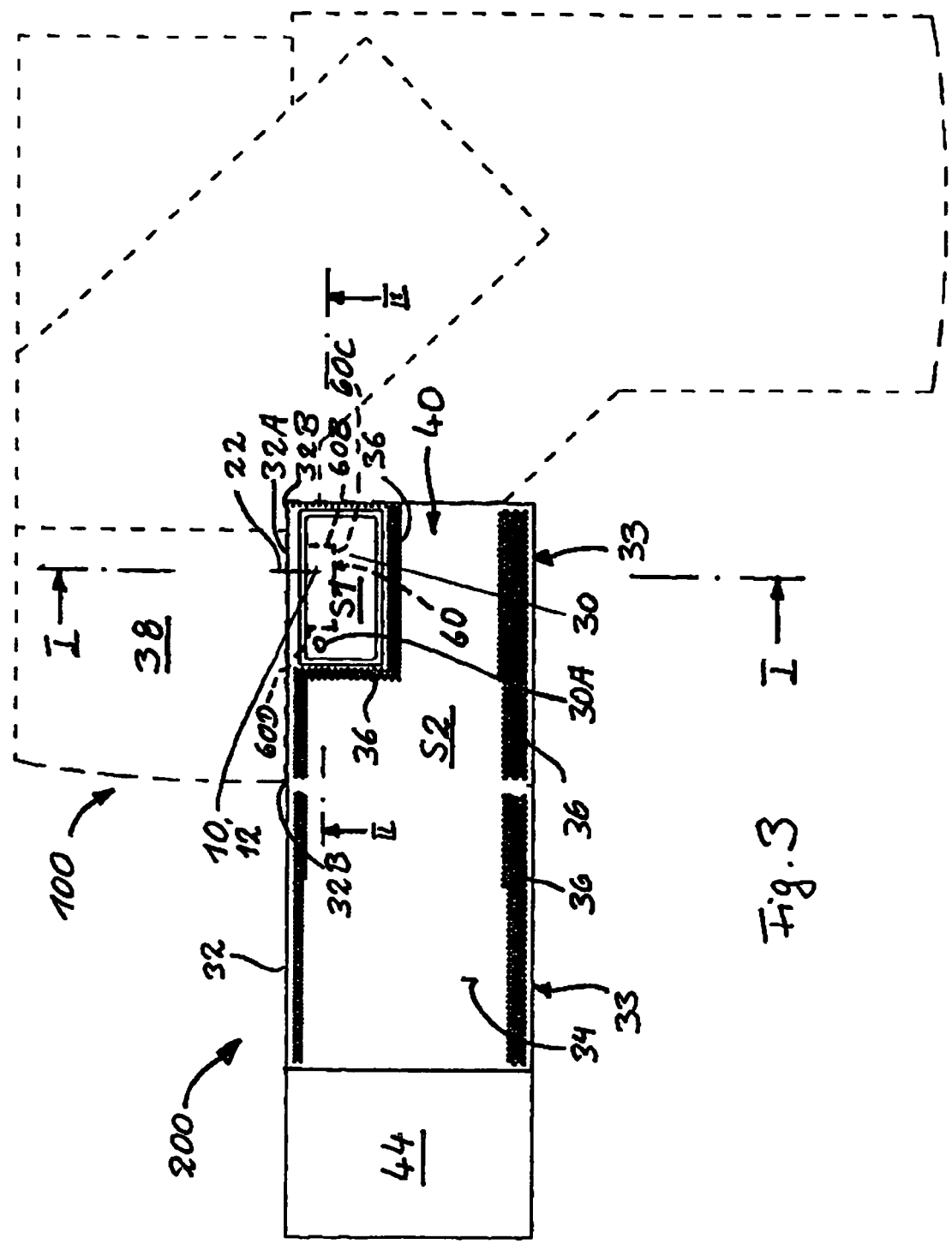
FIG. 3 shows a schematic view of the same device from above of the clean room floor (without funnel) in horizontal section view (section along the line III-III of FIGS. 1 and 2)

The workspace 40 of the class II microbiological safety cabinet (msc) 200, which corresponds to the international standard for safe work with biological working materials, is subdivided into a first safety zone S1 and a second safety zone S2. The elements considered for the droplets and particulate matter formation, that is, for example, the nozzle 12, the deflection device 24, the collection receptacles 21A to 21C, and the collecting funnel 28, are located in the area of the first safety zone S1. The first safety zone S1 and the tray 30 are separated in the floor 34 of the clean room 40 by means of a series of exhaust-air openings 36 from the second safety zone S2 (FIG. 3). A further subdivision of the clean room can be carried out by means of a housing 60, 60A-60D of the sorting head 10, which his open on the bottom. Turbulent air flows, which can influence the sorting via the lower mouth edge of the housing, are suppressed by means of a downwardly directed air suction through the clean room floor.

The housing in coaction with the downwardly directed laminar air flow, which brushes past along the outside of the housing, in connection with the suction flow at the clean room floor, channels the released particulate matter toward the exhaust-air channel.

The sorting head 10 is mounted on a partial wall 32A, which forms a partial surface of a rear wall 32 of the workspace 40 of a microbiological safety cabinet 200 and is vibration-damped from the remaining parts (decoupler 32B).

Figure 4:
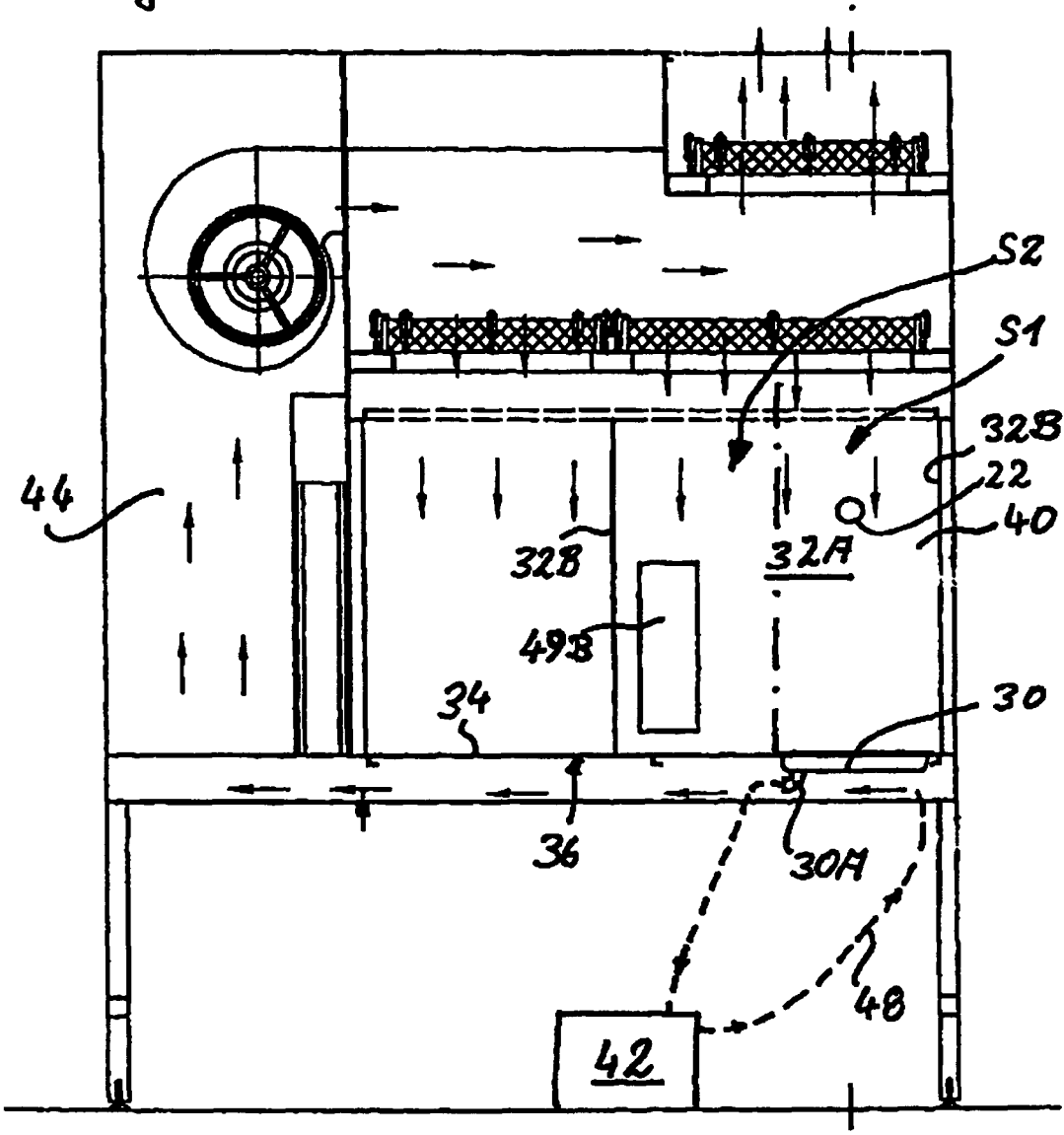
FIG. 4 shows a vertical cross section of the microbiological safety cabinet of the same device in schematic representation and without sorting head.
Figure 5:
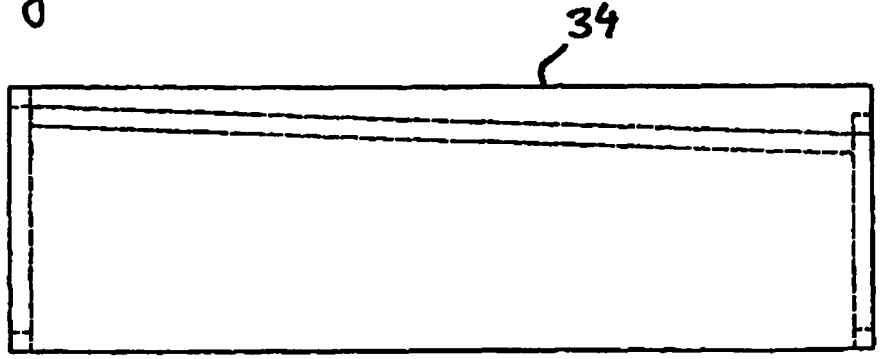
FIG. 5 shows an alternative embodiment of the exhaust-air channel of the same microbiological safety cabinet in front view.

As can be seen in FIG. 4, the microbiological safety cabinet 200 has a laterally elevated suction channel at the front face opposite to the safety zone S1, into which the air drawn off underneath the exhaust air openings 36 in the clean room 34 of the microbiological safety cabinet is introduced in order to additionally retain microparticles via HEPA filters. The suction cross section in the floor 34 of the microbiological safety cabinet 200 narrows toward the suction channel 44, as can be seen in FIG. 3. As an alternative, the channel provided underneath the clean room floor narrows as can be seen in FIG. 5.

Wall feedthroughs, such as, for example, 46A, 46B, allow feeding through signals or signal lines and/or working fluids through one of the housing walls of the clean room of the microbiological safety cabinet. A recirculation line 48 serves for recirculating air, which originates from the suction of waste from the first safety zone S1.

REFERENCE NUMERALS LIST

| | |
|---|---|
| 10 | Sorting head |
| 12 | Exhaust-gas nozzle |
| 14 | Sheath stream |
| 16 | Particle stream |
| 18 | Vibration generator |
| 20 | Sorting stream |
| 20' | Droplet stream |
| 20A | Throughflow |
| 20B/C | Side streams |
| 21A | Suction nozzle |
| 21B | Collection receptacle |
| 21C | Collection receptacle |
| 22 | Monitoring device |
| 22A | Movable seal (bellows) |
| 24 | Deflection device |
| 28 | Collecting funnel |
| 30 | Tray |
| 30A | Suction connection |
| 32 | Rear wall |
| 32A | Partial wall |
| 32B | Vibration decoupler |
| 33 | Access opening |
| 34 | Floor |
| 36 | Suction openings |
| 38 | Evaluation device |
| 40 | Clean room (workspace) |
| 42 | Suction mechanism |
| 44 | Suction channel |
| 46A, B, . . . | Wall feedthroughs |

-continued

| 48 | Recirculation line |
| 49A | Inspection glass |
| 49B | Removable wall part |
| 50 | Sample feeding device |
| 60 | Housing |
| 60A-D | Housing walls |
| 100 | Sorting device |
| 200 | Class II microbiological safety cabinet |
| S1 | First safety zone |
| S2 | Second safety zone |

The invention claimed is:

1. A device for sorting microparticles having a nozzle for supplying a sorting stream consisting of at least one sheath fluid and microparticles entrained therein,
- a sorting head including a vibration generator for dividing the sorting stream into a droplet stream and a deflection device for sorting the droplet stream into a throughflow and at least one side stream in dependence upon signals of an evaluation device,
- the evaluation device for analyzing the microparticle (s) contained in the droplet and for controlling the deflection device,
- a microbiological safety cabinet (msc) having a clean room for both product and personnel protection, the clean room having a top and a bottom and at least the nozzle, the vibration generator, and the deflection device are arranged in the clean room, in which parts of the evaluation device are arranged outside of the clean room, the clean room having an access opening for a user to access the clean room,
- a monitoring device is provided in a side wall of the msc through which the signals of the microparticles generated in the sorting stream are guided to the detectors of the evaluation device located outside of the msc,
- the clean room including a laminar air flow passing therethrough from at least near the top of the clean room to the bottom of the clean room, the clean room floor including suction openings for the laminar flow and the suction openings being in fluid communication with a suction channel,
- the clean room of the msc is divided into a first safety zone, in which the sorting head is accommodated, and a second safety zone,
- the device further comprising a tray, which is located underneath the sorting head.

2. The device of claim 1, wherein the tray is fluidly connected to a suction mechanism.

3. A device for sorting microparticles having a nozzle for supplying a sorting stream consisting of at least one sheath fluid and microparticles entrained therein,
- a sorting head including a vibration generator for dividing the sorting stream into a droplet stream and a deflection device for sorting the droplet stream into a throughflow and at least one side stream in dependence upon signals of an evaluation device,
- the evaluation device for analyzing the microparticle (s) contained in the droplet and for controlling the deflection device,
- a microbiological safety cabinet (msc) having a clean room for both product and personnel protection, the clean room having a top and a bottom and at least the nozzle, the vibration generator, and the deflection device are arranged in the clean room, in which parts of the evaluation device are arranged outside of the clean room, the clean room having an access opening for a user to access the clean room,
- a monitoring device is provided in a side wall of the msc through which the signals of the microparticles generated in the sorting stream are guided to the detectors of the evaluation device located outside of the msc,
- the clean room including a laminar air flow passing therethrough from at least near the top of the clean room to the bottom of the clean room, the clean room floor including suction openings for the laminar flow and the suction openings being in fluid communication with a suction channel,
- the clean room of the msc is divided into a first safety zone, in which the sorting head is accommodated, and a second safety zone,
- the device further comprising a collecting funnel arranged underneath of the sorting head.

4. A device for sorting microparticles having a nozzle for supplying a sorting stream consisting of at least one sheath fluid and microparticles entrained therein,
- a sorting head including a vibration generator for dividing the sorting stream into a droplet stream and a deflection device for sorting the droplet stream into a throughflow and at least one side stream in dependence upon signals of an evaluation device,
- the evaluation device for analyzing the microparticle (s) contained in the droplet and for controlling the deflection device,
- a microbiological safety cabinet (msc) having a clean room for both product and personnel protection, the clean room having a top and a bottom and at least the nozzle, the vibration generator, and the deflection device are arranged in the clean room, in which parts of the evaluation device are arranged outside of the clean room, the clean room having an access opening for a user to access the clean room,
- a monitoring device is provided in a side wall of the msc through which the signals of the microparticles generated in the sorting stream are guided to the detectors of the evaluation device located outside of the msc,
- the clean room including a laminar air flow passing therethrough from at least near the top of the clean room to the bottom of the clean room, the clean room floor including suction openings for the laminar flow and the suction openings being in fluid communication with a suction channel,
- the clean room of the msc is divided into a first safety zone, in which the sorting head is accommodated, and a second safety zone,
- wherein a tray arranged underneath of the sorting head is isolated/separated from the second safety zone by a series of the suction openings.

* * * * *